(12) United States Patent
Jones et al.

US008496034B2

(10) Patent No.: US 8,496,034 B2
(45) Date of Patent: Jul. 30, 2013

(54) METHODS FOR PREDICTING WARP AT A GIVEN CONDITION

(75) Inventors: John E Jones, Seattle, WA (US); Mark A Stanish, Seattle, WA (US); Stanley L Floyd, Enumclaw, WA (US); Susan K Kaluzny, Seattle, WA (US); Thomas J Taylor, Seattle, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 1114 days.

(21) Appl. No.: 11/691,631

(22) Filed: Mar. 27, 2007

(65) Prior Publication Data

US 2008/0243424 A1 Oct. 2, 2008

(51) Int. Cl.
*B23Q 15/00* (2006.01)

(52) U.S. Cl.
USPC .......................................... 144/391; 144/403

(58) Field of Classification Search
USPC .... 144/356, 357; 73/597, 602, 432.3; 702/42, 702/81, 155, 183, 189, 159
See application file for complete search history.

(56) References Cited

U.S. PATENT DOCUMENTS

| 4,563,635 | A * | 1/1986 | Wagner et al. ................ 324/688 |
| 6,293,152 | B1 * | 9/2001 | Stanish et al. .................. 73/597 |
| 6,305,224 | B1 * | 10/2001 | Stanish et al. .................. 73/597 |
| 6,308,571 | B1 * | 10/2001 | Stanish et al. .................. 73/597 |
| 6,598,477 | B2 * | 7/2003 | Floyd .............................. 73/597 |
| 6,996,497 | B2 * | 2/2006 | Floyd et al. .................... 702/181 |
| 7,017,413 | B2 * | 3/2006 | Floyd et al. ...................... 73/597 |
| 7,043,990 | B2 * | 5/2006 | Wang et al. ...................... 73/597 |
| 7,266,461 | B2 * | 9/2007 | Huang et al. ..................... 702/42 |
| 7,324,904 | B2 * | 1/2008 | Floyd et al. ...................... 702/81 |
| 7,406,190 | B2 * | 7/2008 | Carman et al. ................ 382/141 |

FOREIGN PATENT DOCUMENTS

EP   1 589 339 A1   10/2005

OTHER PUBLICATIONS

Stanish, M.A., "Predicting the Crook Stability of Lumber within the Hygroscopic Range", Drying Technology, 2000, Taylor & Francis, Philadelphia, PA Us (XP009081241).
Eastin, I.L., Shook, S.R., Fleishman, S.J., Material substitution in the U.S. residential construction industry, 1994 versus 1988, Forest Products Journal, vol. 51, No. 9, 31-37.
Wood Handbook, General Technical Report 113 (1999) Department of Agriculture, Forest Service, Forest Products Laboratory.
Hastie, T., Tibshirani, R., and Friedman, J., (2001) The Elements of Statistical Learning, Springer, New York.

* cited by examiner

*Primary Examiner* — David Walczak
*Assistant Examiner* — Jennifer C Chiang
(74) *Attorney, Agent, or Firm* — Christensen O'Connor Johnson Kindness PLLC

(57) ABSTRACT

Methods are provided for predicting warp of a lumber product at a given condition, such as relative humidity, temperature, moisture content, or the like. Note that this methodology may apply to any of crook, bow, twist, cup, or combinations of these quantities. The method involves measuring an original warp of a first wood product at a known condition; changing the condition of the first wood product to a new condition; measuring a second warp of the first wood product at the new condition; developing a prediction model based on data from the original warp and condition and the second warp; measuring an original warp and condition of the given wood product; and inputting data from the original warp and condition of the given wood product to the prediction model to determine warp at a given condition.

14 Claims, 3 Drawing Sheets

METHODS FOR PREDICTING WARP AT A GIVEN CONDITION

FIELD OF THE INVENTION

This invention relates generally to methods for predicting the warp of a lumber product at a given condition, such as, for example, moisture content or relative humidty.

BACKGROUND OF THE INVENTION

Wood products, such as logs, boards, other lumber products, or the like, can be graded or classified into qualitative groups by the amount of warp potential, or dimensional stability, in the product. Crook, bow, twist, and cup are examples of warp and are illustrated in FIG. 1. The groups are used to qualitatively represent the warp state at a specified ambient condition or the degree of warp instability of a wood product. The qualitative groups are typically ordinal in nature, though nominal categories may also be used.

The degree of warp depends on several known factors, such as density, modulus of elasticity (hereinafter referred to as "MOE"), moisture content variation, pith location, compression wood, grain angle and others. Many of these factors can be quantitatively or qualitatively evaluated with different types of sensors. For example, MOE can be estimated from the propagation of sound through wood, and specific gravity can be estimated from the capacitance of wood. A different type of sensor group or system may be utilized for detecting each of these properties.

During the three year period from 1995 to 1998, solid sawn softwood lumber usage in wall framing, floor framing and roof framing dropped by 9.9%, 17.2% and 11% respectively in the United States (Eastin et al., 2001)[1]. In this survey of nearly 300 builders, lumber straightness was rated the most important factor affecting buying decisions; yet of all the quality attributes surveyed, dissatisfaction with straightness was highest. It is generally recognized that softwood lumber will continue to lose market share unless the industry improves the in-service warp stability of its product.

[1]Eastin, I. L., Shook, S. R., Fleishman, S. J., Material substitution in the U.S. residential construction industry, 1994 versus 1988, *Forest Products Journal*, Vol. 51, No. 9, 31-37.

In the United States, most softwood dimension lumber is visually graded for a variety of attributes that affect its appearance and structural properties. These attributes include knots, wane, dimension (thickness, width, and length), decay, splits and checks, slope-of-grain, and straightness (warp). Strict quality control practices overseen by third party grading agencies are in place to ensure that all lumber is "on-grade" at the point the grade is assigned. Unfortunately, the straightness and dimension of a piece are not static and can change after the piece is graded. Additional warp and size change can develop after the piece is in the distribution channel or after it is put into service. Typical moisture content of fresh kiln dried lumber averages 15% but ranges from 6% to 19%. This lumber will eventually equilibrate to a moisture ranging from 3% to 19% depending on time of year, geography and whether the application is interior or exterior (Wood Handbook)[2]. This moisture change results in changes in both dimension and warp properties. Any piece of lumber is prone to develop additional "in-service" warp if a) its shrinkage properties are not uniform and it changes moisture or b) its moisture content is not uniform at the point the original grade was assigned. Neither of these conditions is detectable with traditional visual grading methods. Customers of wood products seek stability in both dimension and warp properties.

[2] Wood Handbook, General Technical Report 113 (1999) Department of Agriculture, Forest Service, Forest Products Laboratory.

The wood handbook[2] provides guidelines for assessing the width and thickness stability of solid sawn lumber. Average thickness and width shrinkage is governed by grain orientation as well as radial and tangential shrinkage properties. These average radial and tangential shrinkage values vary by species and are reduced if heartwood is present. Although these methods can be used to estimate the average thickness and width shrinkage behaviour of a species, methods for precise quantification do not exist. There are even fewer design tools for estimating length shrinkage.

[2] Wood Handbook, General Technical Report 113 (1999) Department of Agriculture, Forest Service, Forest Products Laboratory.

Today the patterns of equilibrium moisture and shrinkage coefficients within a full size lumber product can be accurately measured only in a laboratory environment. The laboratory technique involves cutting the piece of lumber into small "coupons" and measuring the moisture content and shrinkage coefficients using ASTM standards D-4492 and D-143, respectively. Although much is known about equilibrium moisture and shrinkage behaviour of wood, there are as yet no comprehensive theoretical models and no methods of monitoring these properties in a real time production environment.

However, it has been empirically noted that the amount of warp in a lumber product at one moisture content or environmental condition is typically highly correlated with the warp of the same piece of lumber at a different moisture content. In some applications this correlation may be sufficient to identify pieces of lumber that are projected to meet certain end-use requirements for dimensional stability

BRIEF DESCRIPTION OF THE DRAWINGS

The embodiments of the present invention are described in detail below with reference to the following drawings.

DETAILED DESCRIPTION OF THE INVENTION

The present invention generally relates to methods for predicting warp of a lumber product at a given condition, such as moisture content, relative humidity, temperature, or the like using only an initial warp measurement and a measureable condition, such as moisture content. Note that this methodology may apply to any of crook, bow, twist, cup, or combinations of these quantities. In the embodiments provided below, these modes of dimensional instability will generally be referred to as "warp".

In an embodiment, a method is provided for predicting warp of a given wood product. The method has a first step of measuring an original warp of a first wood product at a known condition. The condition may be at least one of relative humidity, temperature, moisture content, or the like. In a next step, the condition of the first wood product is changed to a new condition. A second warp is measured of the first wood product at the new condition. A prediction algorithm is then developed based on data from the original warp and condition, and the second warp. The given wood product, from which a warp prediction will be made, is then measured for original warp and condition data. This data is inputted to the prediction algorithm to estimate warp at a given condition.

In another embodiment, a first step may be creating an algorithm. This may be accomplished by collecting a sample of lumber, such as a board or other wood product taken from a log. The warp of the board may be measured along with the current moisture content. These measurements could be conducted in a lab, or on-line during production. Next, the moisture content of the board may be changed. In an embodiment, this may be performed via drying in a kiln. The new warp and new moisture content are then recorded.

Next, a prediction model or algorithm is determined. This prediction model may be used to 1) predict warp as a function of moisture content, or 2) predict end-point warp as a function of initial warp and initial moisture content or 3) predict end-point warp as a function of initial warp, initial moisture content and end-point moisture content.

In a next step, the warp and moisture content on a given piece of lumber are measured. These measured values are used as inputs to the prediction model or algorithm to obtain a warp prediction. It should be noted that the inputs for the prediction model may include, in an embodiment, only warp and moisture content, or, in an embodiment, may additionally include desired end-point moisture content. In another embodiment, the lumber may be sorted based on predictions.

The present invention may be better understood by the following example:

Example 1

Figure 1:
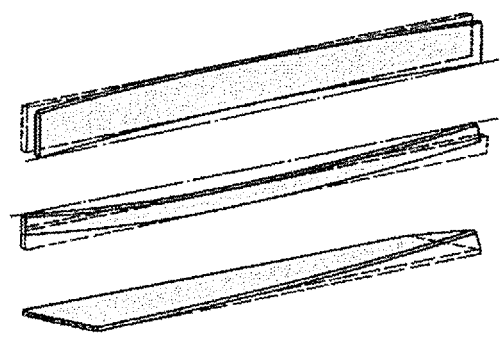
FIG. 1 provides examples of crook, bow, twist, and cup in a wood product.
Figure 2:
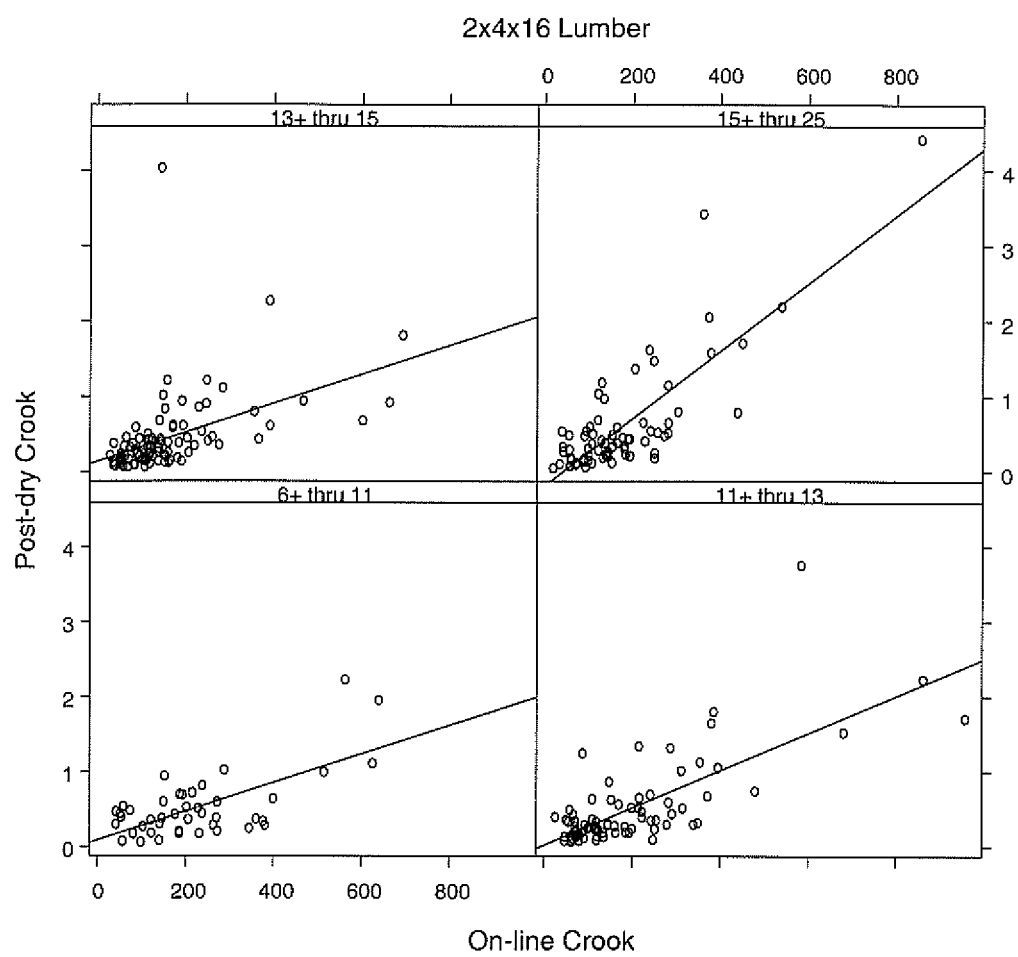
FIG. 2 is a plot of post-drying crook versus on-line crook in an embodiment of the present invention.

This example is taken from an actual pilot-trial at Plymouth, N.C. A sample of several hundred pieces of lumber, representing several dimensions, was collected at a Weyerhaeuser planer mill over the course of several months. On-line measurements of warp and moisture content were saved and stored in a database. On-line measurements are those that are made and recorded during the manufacturing process. The sampled lumber was taken to a laboratory facility where each piece of lumber was dried in an RF dryer, allowed to equilibrate, and then re-measured for warp and moisture content. These data were also stored in the database, so that each board had two warp measurements at two different moisture contents—one made on-line during manufacturing, and one made after drying in the lab; the former are referred to as the "on-line" measurements and the later are referred to as the "off-line" or "post-drying" measurements. FIG. 2 is a plot of the post-drying crook versus the on-line crook. The data are separated into different panels by their value of on-line moisture content. For example, the lower-left panel shows all boards with an on-line moisture content between 6% and 11%.

Figure 3:
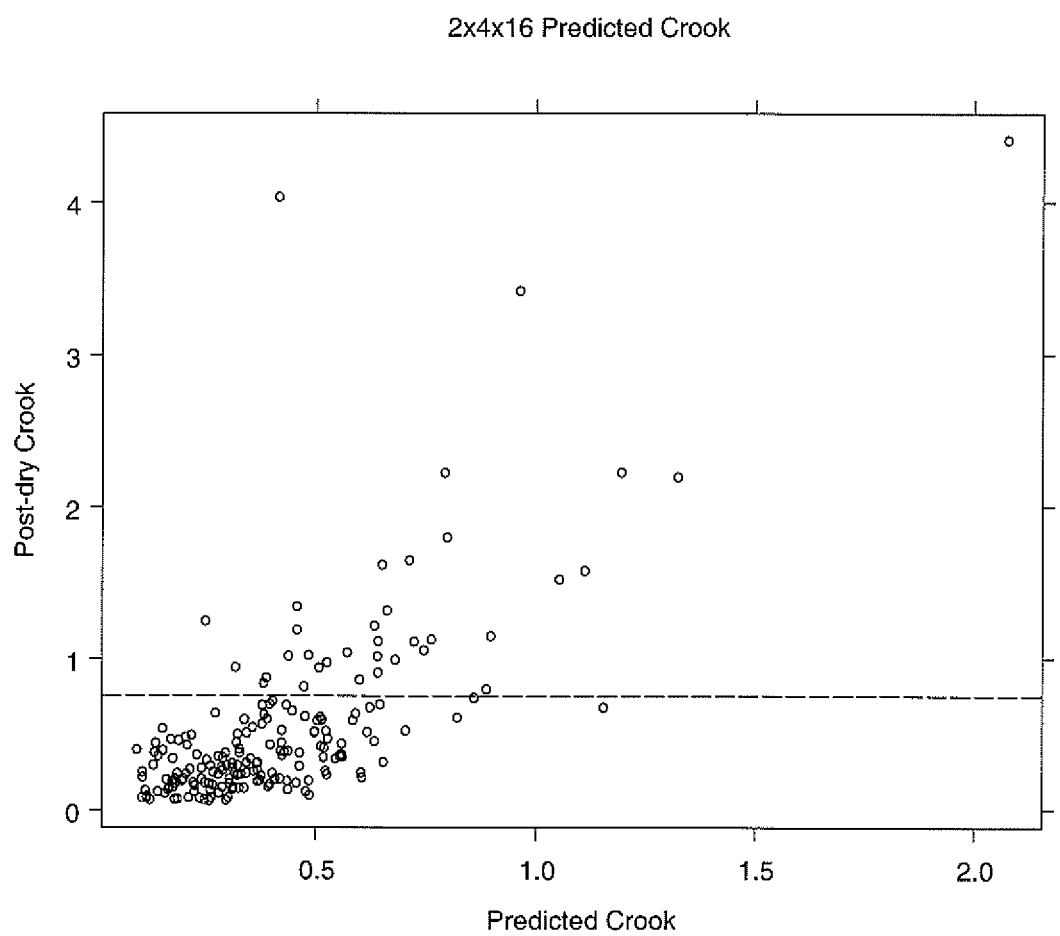
FIG. 3 is a plot of the results of a crook model for 2 inch by 4 inch by 16 inch boards in an embodiment of the present invention.

FIG. 2 suggests that the post-drying crook measurement is strongly associated with the on-line crook measurement, and that this association depends upon the on-line moisture content. Similar associations are also seen with both bow and twist. The data described above were used to create regression models for crook, bow, and twist. In this example, the regression models were used to obtain a warp prediction, however warp prediction algorithms are not limited to regression models, and many other prediction methods exist, as is well known in the art. Examples include, but are not limited to Neural networks, Boosting-methods, recursive partitioning trees, kernel methods, and others. FIG. 3 shows the results of the crook model for 2 inch by 4 inch by 16 inch boards; the y-axis is the measured value of post-dry crook and the x-axis is the predicted crook value. The horizontal dashed line in FIG. 3 shows the No. 1 grade limit for crook. Here we can see that nearly all boards with a predicted value less than 0.25 stayed under the No. 1 grade limit after drying. Models were also developed for both bow and twist, showing similar results.

The prediction models described above were then included in an on-line sort algorithm for a Weyerhaeuser planer mill. The algorithm took on-line measurements of warp and moisture content, passed these values to the models to get crook, bow and twist predictions, then sorted the lumber on-line using thresholds for the predicted warp values.

In practice, one might expect to sort for "warp-stable" lumber, or potentially unstable lumber, in a similar manner to that described in this example. However, there could also be other uses for the warp predictions such as improving on-line grading or in rip-and-trim decisions.

In other embodiments, the two conditions at which warp are measured on a lumber product may be defined by any one or more of moisture content, relative humidity, or temperature. An example of such an alternative embodiment would be similar to the example given above, but where the lumber product was conditioned to a known relative humidity and temperature, rather than dried to a measurable moisture content. In this case, one might be interested in predicting warp at this relative humidity and temperature condition, or alternatively to predict warp to an equilibrium moisture content associated with the relative humidity and temperature. Moreover, other embodiments are contemplated in which any of the conditions may be associated with any of the other conditions described herewith, such that the condition for which an original warp is measured (for an original wood product used to create a prediction model) is not the same condition by which warp is predicted.

The methods for determining warp stability or any of the other properties mentioned above may involve the use of single and/or multiple sensor group systems to provide qualitative and/or quantitative estimates. The measurements may be taken at one, or more sections of the wood product (i.e., log or board), which may differ in size given a particular embodiment. The properties observed at the one or more sections may allow a qualitative and/or quantitative estimate of dimensional stability of a region of interest. In a first embodiment, the region of interest may overlap with one or more sections of the wood product. In another embodiment, the region of interest may be the entire wood product. In yet another embodiment, the region of interest may be the same as the one or more sections detected by the sensor group(s). In another embodiment, the region of interest does not have an overlap with the one or more sections. The dimensional stability assessed may be cup, crook, bow, twist, length stability, thickness stability, width stability, or any combination of these.

In an embodiment of the present invention, a classification algorithm may be created to classify a wood product into one of a plurality of groups or categories. The groups may be based on qualitative or quantitative characteristics. For example, in an embodiment, the categories may be different grades. Warp classification of wood products, such as boards may require inputs from one or more sensor groups detecting the original warp and original moisture content or environmental condition of the boards. The sensor groups may be a part of those systems previously mentioned for analyzing a wood product. The technologies for these systems are known by those skilled in the art. For example, the sensor groups may obtain moisture content measurement, electrical property measurement, structural property measurement, acousto-ultrasonic property measurement, shape measurement, and spectral measurement. Acousto-ultrasonic property measurement measures may measure velocity and/or damping. The spectral measurement may be characterized by absorption or reflectance values over a wavelength spectrum ranging from ultraviolet through near infrared.

Using this approach, the prediction model or algorithm of the present invention may use inputs of many different resolution scales. Some examples are board average dielectrical properties, moisture content measured across the width of the board in one foot increments along the length of the board, spectroscopy data collected every inch, or laser data collected every ¼ inch.

The inputs are functions of the sensor signals and may be either quantitative or qualitative. For example, an input could be the estimated moisture content for each 12 inch lineal section of a piece of lumber, as estimated by a moisture meter. Inputs may be direct sensor measurements pre-processed signals, combined signals from several sensors or predicted measures from other sensors. Signal pre-processing may include, but is not limited to, such steps as filtering, smoothing, derivative calculations, power spectrum calculations, Fourier transforms, etc., as is well known in the art. Predicted measurements from other sensors may include, but are not limited to, moisture content predicted from sensors which measure the light scattering and light absorption properties of wood and used as inputs to a partial least squares, or "PLS", prediction model.

The prediction algorithm(s) or model(s) based on the set of inputs can be derived using many techniques which include, but are not limited to, regression trees, classification trees, linear discriminant analysis, quadratic discriminant analysis, logistic regression, Partial Least Squares or other supervised learning techniques such as neural networks. There are many forms of equations or algorithms that could be used, and a general reference is Hastie, et al[3].

[3] Hastie, T., Tibshirani, R., and Friedman, J., (2001) The Elements of Statistical Learning, Springer, New York.

These algorithms can be developed to classify boards into 2 or more groups. For example, boards might be classified into four grades (#1 grade, #2 grade, #3 grade, #4 grade) or into two classifications like warp stable and warp unstable, or into three categories like crook less than 0.25 inches, crook between 0.25 and 0.5 inches, crook greater than 0.5 inches. Typically, the parameters in the models or algorithms are derived from a training-set of data and the performance is tested on a testing-set of data before being used in production, although other approaches exist.

In a first embodiment, two or more sensor groups may provide two or more inputs to a classification algorithm to classify wood products into one of a plurality of categories. Where one or more sensor group was used to measure the initial warp of a lumber product and one or more sensor group was used to measure the initial moisture content or environmental condition of the lumber product.

In a second embodiment, two or more sensor groups may provide two or more inputs to an algorithm for providing a quantitative assessment of dimensional stability of wood products. Where one or more sensor group was used to measure the initial warp of a lumber product and one or more sensor group was used to measure the initial moisture content or environmental condition of the lumber product.

In a third embodiment, two or more sensor groups may provide two or more inputs to a classification algorithm to classify wood products into one of a plurality of categories. Next, a second algorithm may be selected after classifying the wood product. This second algorithm may be selected from a plurality of algorithms which are used to assess the dimensional stability in a quantitative manner.

Other methods for determining warp stability, wane, moisture, knot properties, or the like for a log or board are contemplated, including those described in U.S. Pat. Nos. 6,308,571; 6,305,224; and 6,293,152 to Stanish et al., or any other known methods currently used at mill sites. These methods could be implemented into the process steps described above.

While the embodiments of the invention have been illustrated and described, as noted above, many changes can be made without departing from the spirit and scope of the invention. Accordingly, the scope of the invention is not limited by the disclosure of the embodiments. Instead, the invention should be determined entirely by reference to the claims that follow.

What is claimed is:

1. A method for sorting two or more given wood products, the method comprising the steps of:
    measuring original warp of at least one first wood product at a known or measured moisture content;
    changing the moisture content of the at least one first wood product to a new moisture content;
    measuring a second warp of the at least one first wood product at the new moisture content;
    developing a prediction algorithm based on data from the original warp and the second warp and at least one of the original and new moisture contents;
    measuring an original warp and moisture content for each of the two or more given wood products;
    inputting data from the original warp and at least one of the original and given moisture contents from each of the two or more given wood products to the prediction algorithm to predict a predicted warp for each of the two or more given wood products at a given moisture content; and
    sorting the two or more given wood products based on the predicted warp at the given moisture content.

2. The method of claim 1 wherein the original warp is measured based on one or more inputs and/or the original moisture content is measured based on one or more inputs.

3. The method of claim 2 wherein the inputs are selected from a group consisting of: moisture content measurement, camera imaging, laser range finding, acoustic range finding, mechanical displacement, electrical property measurement, infra-red or near infra-red measurement, acousto-ultrasonic property measurement, shape measurement, weight, nuclear magnetic resonance measurement, temperature, and microwave measurement.

4. The method of claim 1 wherein the prediction model is derived using at least one of the following techniques: regression trees, classification trees, linear discriminant analysis, quadratic discriminant analysis, logistic regression, Partial Least Squares and neural networks, linear regression, non-linear regression, generalized linear regression, generalized additive regression, projection pursuit regression, or look-up tables.

5. The method of claim 1 wherein the warp is characterized quantitatively.

6. The method of claim 1 wherein the warp is characterized qualitatively.

7. The method of claim 1 wherein the warp is at least one of: crook, bow, cup, and twist.

8. A method for sorting two or more given wood products, the method comprising the steps of:
    measuring original warp of at least one first wood product, wherein the at least one first wood product has at least two known or measured conditions, the at least two known or measured conditions being selected from: moisture content, relative humidity and temperature;

changing at least one of the at least two known conditions of the at least one first wood product to a new condition;

measuring a second warp of the at least one first wood product at the new condition;

developing a prediction algorithm based on data from the original warp and the second warp and at least one of the original and new conditions;

measuring an original warp and condition for each of the two or more given wood products;

inputting data from the original warp and at least one of the original and given conditions from each of the two or more given wood products to the prediction algorithm to predict a predicted warp for each of the two or more given wood products at a given condition; and sorting the given wood product based on the predicted warp at the given condition.

9. The method of claim 8 wherein the original warp is measured based on one or more inputs and/or the original moisture content is measured based on one or more inputs.

10. The method of claim 9 wherein the inputs are selected from a group consisting of: moisture content measurement, camera imaging, laser range finding, acoustic range finding, mechanical displacement, electrical property measurement, infra-red or near infra-red measurement, acousto-ultrasonic property measurement, shape measurement, weight, nuclear magnetic resonance measurement, temperature, and microwave measurement.

11. The method of claim 8 wherein the prediction algorithm is derived using at least one of the following techniques: regression trees, classification trees, linear discriminant analysis, quadratic discriminant analysis, logistic regression, Partial Least Squares and neural networks, linear regression, non-linear regression, generalized linear regression, generalized additive regression, projection pursuit regression, or look-up tables.

12. The method of claim 8 wherein the warp is characterized quantitatively.

13. The method of claim 8 wherein the warp is characterized qualitatively.

14. The method of claim 8 wherein the warp is at least one of: crook, bow, cup, and twist.

* * * * *